US00PP21621P2

(12) United States Plant Patent
Sanders

(10) Patent No.: US PP21,621 P2
(45) Date of Patent: Jan. 11, 2011

(54) ***IMPATIENS* PLANT NAMED 'IMTRACORBU'**

(50) Latin Name: *Impatiens walleriana*
Varietal Denomination: Imtracorbu

(75) Inventor: Monica Maria Adelheid Sanders, Grootebroek (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/587,348

(22) Filed: Oct. 6, 2009

(51) Int. Cl.
*A01H 5/00* (2006.01)

(52) U.S. Cl. ..... Plt./317

(58) Field of Classification Search ..... Plt./317
See application file for complete search history.

*Primary Examiner*—June Hwu
(74) *Attorney, Agent, or Firm*—S. Matthew Edwards

(57) ABSTRACT

A new *Impatiens* plant named 'Imtracorbu,' characterized particularly as to novelty by a flat and strong outward spreading growth habit, freely branching with branches that tend to grow horizontally, resulting in a big and floriferous plant with large red-purple flowers with a light red blotch.

1 Drawing Sheet

Latin name of the genus and species of the plant claimed: *Impatiens walleriana.*

Varietal denomination: 'Imtracorbu'.

BACKGROUND OF THE NEW PLANT

The present invention comprises a new distinct cultivar of *Impatiens,* botanically known as *Impatiens walleriana.*

The new *Impatiens* is a product of a planned breeding program conducted in Enkhuizen, Netherlands. The new *Impatiens* cultivar has a flat and spreading growing type, is floriferous with large pink salmon flowers with a very distinct blotch in the flower, and has attractive dark green foliage.

The present cultivar originated from a cross-pollination made in 2005, of a proprietary *Impatiens walleriana* selection identified as 'X5129-3,' not patented, as the female, or seed parent, with a proprietary *Impatiens walleriana* selection identified as 'W3797-3,' not patented, as the male, or pollen parent.

The present cultivar has been repeatedly asexually reproduced by cuttings in Enkhuizen, Netherlands, in Angers, France, and in Gilroy, Calif., USA over a four year period. The new variety is stable and reproduces true to type in successive generations of asexual reproduction. It takes 6 to 8 weeks to produce a finished plant, depending on the temperature.

This new *Impatiens* plant is an annual in most climatic zones in the US, except in zones 9 and 10, where it is a perennial plant.

DESCRIPTION OF THE DRAWING

This new *Impatiens* plant is illustrated by the accompanying photographic drawing which shows blooms, buds and foliage of the plant in full color, the color showing being as true as can be reasonably obtained by conventional photographic procedures.

BOTANICAL DESCRIPTION OF THE PLANT

The following detailed descriptions set forth the distinctive characteristics of this new *Impatiens*. The data which defines these characteristics were collected from asexual reproductions carried out in Enkhuizen, Netherlands. The plant history was taken on 27 week old plants blossomed under natural light in the field.

Color readings were taken in the office under ambient light. Color references are primarily to The R.H.S. Colour Chart of the Royal Horticultural Society of London.

Plants of the new *Impatiens* differ primarily from the plants of the female parent selection in the following characteristics:

Plants of the new *Impatiens* have pink salmon flowers with a distinct dark blotch and short flower stems, whereas the plants of the female parent have light salmon flowers with a small blotch and long flower stems.

Plants of the new *Impatiens* differ primarily from the male plant selection in the following characteristics:

Plants of the new *Impatiens* have male sterile flowers, flowers are pink salmon with distinct dark blotch and a good spreading habit, whereas the plants of the male parent have male fertile flowers, flowers are light salmon with a small blotch and a compact habit.

TABLE 1

DIFFERENCES BETWEEN THE NEW CULTIVAR 'IMTRACORBU' AND A SIMILAR CULTIVAR

| | 'Imtracorbu' | 'Imtrarepu' (U.S. Plant Pat. No. 17,111) |
|---|---|---|
| Flower color: | Pink salmon with distinct blotch | Pink |
| Flower size: | Large | Medium |

The family relationship is as follows:

The female parent line of 'Imtracorbu' is 'RBGE 19821569'×'J0475-2' crossed with line 'M170' and crossed with line 'S158.'

The plant:

*Parentage.*—

*Female parent.*—'X5129-3,' not patented.

*Male parent.*—'W3797-3,' not patented.

Propagation:

*Type cutting.*—Terminal cuttings.

*Time to initiate roots.*—10-12 days at 20° C.

*Time to produce a rooted cutting.*—4 weeks.
*Root description.*—Fine, fibrous, and white in color.

Plant description:
*General appearance.*—Makes long branches that tend to grow horizontally.
*Growth and branching habit.*—Freely branching habit, freely flowering, vigorous.
*Plant height.*—40 cm.
*Plant spread.*—80 cm.

Lateral branch description:
*Length.*—19-45 cm.
*Diameter.*—8 mm.
*Texture.*—Smooth, glabrous.
*Internode length.*—3.1 cm.
*Color.*—RHS N146A with anthocyan colouring RHS 182A.

Foliage description:
*Arrangement.*—Alternate.
*Length, mature leaves.*—6.5 cm.
*Width, mature leaves.*—3 cm.
*Shape.*—Oblong-ovate.
*Apex.*—Acuminate.
*Base.*—Acute.
*Margin.*—Crenate.
*Texture, upper surface.*—Smooth, glabrous.
*Texture, lower surface.*—Smooth, glabrous.
*Venation pattern.*—Pinnate.
*Color young foliage, upper surface.*—RHS 143A.
*Color young foliage, lower surface.*—RHS 143C.
*Fully expanded foliage, upper surface.*—RHS 137A.
*Fully expanded foliage, lower surface.*—RHS 137C.
*Venation, upper surface.*—RHS 143A.
*Venation, lower surface.*—RHS 143A.
*Petiole, length.*—About 1.5 cm.
*Petiole, diameter.*—About 2 mm.
*Texture.*—Smooth, glabrous.
*Color.*—RHS 199D.

Flower description:
*Flower type and flowering habit.*—Single.
*Number of flowers per leaf axil.*—3.
*Number of flowers and flower buds per lateral branch.*—24.
*Flower position.*—Above and beyond the foliage and typically facing upwards and outward.
*Flower shape.*—Rounded, mostly flat.
*Flowers lasting.*—About 7-9 days on the plant depending on environmental conditions.
*Flowers.*—Non persistent.
*Flowers.*—Not fragrant.
*Flowering.*—Indeterminate and continuous.
*Flowering season.*—Year round under greenhouse conditions. In the garden, flowering from spring until fall.
*Flower diameter.*—About 5 cm.

Flower buds:
*Rate of opening.*—From flower bud to fully open flower, typically about 6-8 days, depending on temperature.
*Bud length* (*at stage of showing color*).—About 1.1 cm.
*Bud diameter.*—About 0.8 cm.
*Bud shape.*—Ovoid.
*Texture.*—Smooth, glabrous.
*Color, just before opening.*—RHS 145D.

Petals:
*Quantity.*—Single, five per flower, imbricate.
*Length of banner petal.*—About 2.2 cm.
*Width of banner petal.*—About 2.5 cm.
*Length lateral and basal petals.*—About 2.3 cm.
*Width lateral and basal petals.*—About 2.2 cm.
*Lateral and basal petal shape.*—Obovate.
*Banner petal shape.*—Obovate.
*Petal apex.*—Retuse to emarginate.
*Petal base.*—Attenuate.
*Petal margin.*—Entire.
*Petal texture, upper surface.*—Smooth, satiny.
*Petal texture, lower surface.*—Smooth, satiny.
*Petal color.*—Upper surfaces: Banner petal: RHS 62B with RHS 43B blotch. Lateral petals: RHS 62B with RHS 43B blotch. Basal petals: RHS 62B with RHS 43B blotch. Lower surface when opening and fully opened: All petals are RHS N155B.

Sepals:
*Lateral sepals.*—2.
*Shape.*—Ovate-lanceolate.
*Apex.*—Acute.
*Margin.*—Entire.
*Length.*—3-7 mm.
*Texture upper and lower surface.*—Smooth, glabrous.
*Color.*—RHS 143C.

Spur:
*Length of spur.*—About 2.5 cm.
*Texture of spur.*—Smooth, glabrous.
*Aspect.*—Curved.
*Color of spur.*—RHS 145C.

Peduncles:
*Length of peduncles.*—About 1.6 cm.
*Diameter.*—0.1 cm.
*Aspect.*—About 45 degrees from the stem.
*Color.*—RHS 145B.
*Bracts.*—At least 2.
*Shape.*—Linear-lanceolate.
*Apex.*—Acute.
*Length.*—3-6 mm.
*Color.*—RHS 146C.

Reproductive organs:
*Androecium.*—Stamen number: Five fused at anthers, filaments free, hooded. Anther shape: Oval. Anther length: About 1 mm. Anther color: RHS 58A. Amount of pollen: No pollen.
*Gynoecium.*—Pistil number: One. Pistil length: About 1 mm. Stigma shape: Columnar, five segmented. Stigma color: RHS 184C. Style color: RHS 62A. Ovary arrangement: Five celled. Ovary color: RHS 141A.

Seed development: Seed development has not been observed to date.

Disease/pest tolerance: No known susceptibility to disease or insects noted to date.

What is claimed is:

1. A new and distinct cultivar of *Impatiens* plant named 'Imtracorbu,' as substantially illustrated and described herein.

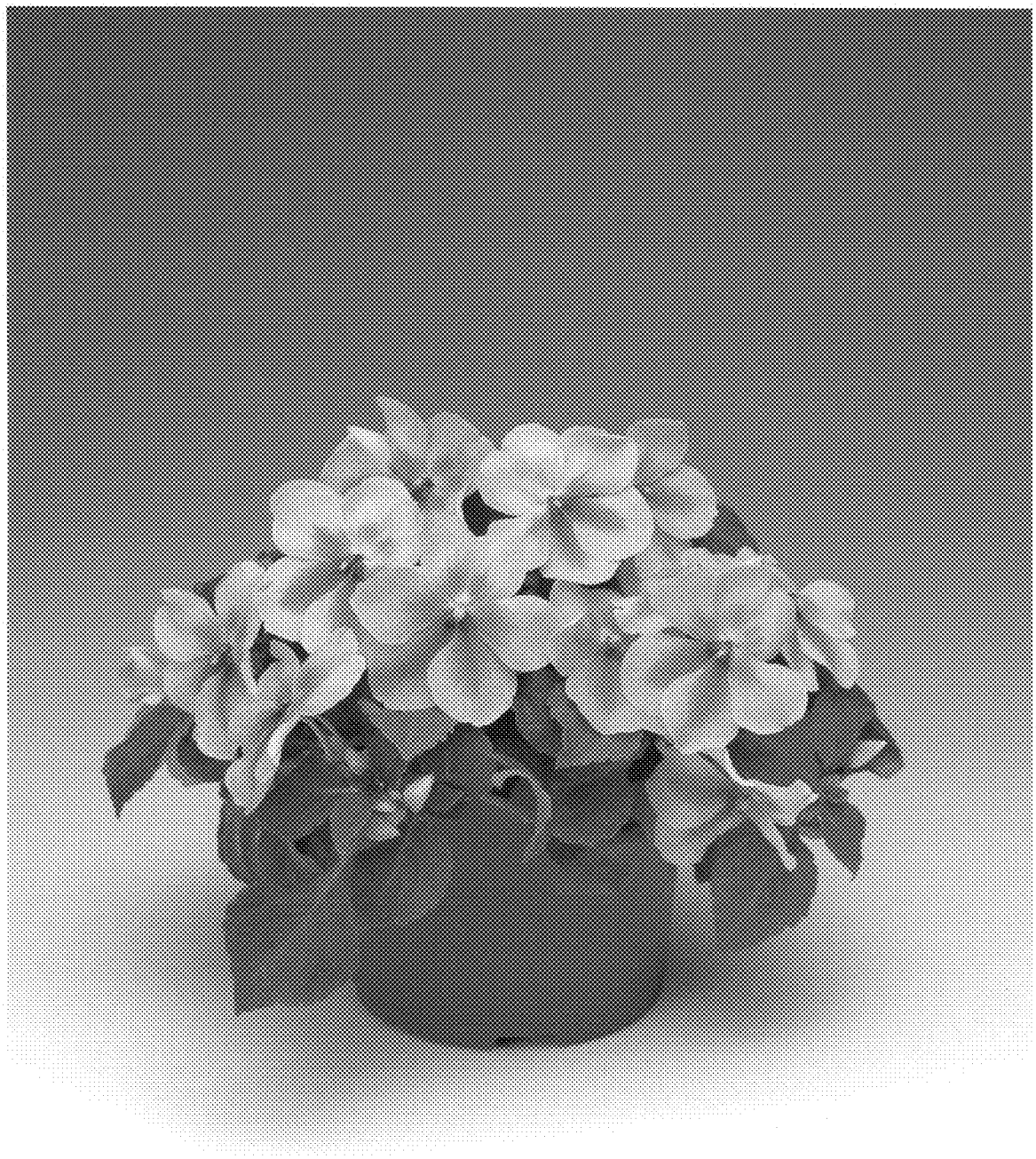

* * * * *